United States Patent
DeJong et al.

(10) Patent No.: US 6,752,762 B1
(45) Date of Patent: Jun. 22, 2004

(54) METHOD AND APPARATUS FOR ULTRASOUND CONTRAST IMAGING

(75) Inventors: Nico DeJong, Krimpen aan den Ijssel (NL); Peter J. Frinking, Geneva (CH)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/869,363

(22) PCT Filed: Jan. 19, 2000

(86) PCT No.: PCT/GB00/00115

§ 371 (c)(1),
(2), (4) Date: Oct. 1, 2001

(87) PCT Pub. No.: WO00/42916

PCT Pub. Date: Jul. 27, 2000

(Under 37 CFR 1.47)

(30) Foreign Application Priority Data

Jan. 21, 1999 (GB) .............................................. 9901270

(51) Int. Cl.[7] .................................................. A61B 8/00
(52) U.S. Cl. .................................................... 600/458
(58) Field of Search ........................ 600/437, 440–441, 600/443, 447, 458; 367/7, 11; 73/618, 620–621, 625–626, 600; 424/9.52; 310/328

(56) References Cited

U.S. PATENT DOCUMENTS

| | | | | |
|---|---|---|---|---|
| 5,410,205 A | * | 4/1995 | Gururaja | 310/328 |
| 5,724,976 A | * | 3/1998 | Mine et al. | 600/459 |
| 5,740,128 A | | 4/1998 | Hossack et al. | |
| 5,833,613 A | * | 11/1998 | Averkiou et al. | 600/440 |
| 5,833,615 A | | 11/1998 | Wu et al. | |
| 6,206,833 B1 | * | 3/2001 | Christopher | 600/443 |
| 6,302,845 B2 | * | 10/2001 | Shi et al. | 600/438 |
| 6,514,209 B1 | * | 2/2003 | Basude et al. | 600/458 |
| 6,532,819 B1 | * | 3/2003 | Chen et al. | 73/606 |

FOREIGN PATENT DOCUMENTS

| | | |
|---|---|---|
| EP | 770 352 | 5/1997 |
| WO | WO 91/15999 | 10/1991 |
| WO | WO 99/35967 | 7/1999 |

* cited by examiner

Primary Examiner—Francis J. Jaworski

(57) ABSTRACT

An apparatus and method for providing an ultrasonic image of an object by use of subharmonic acoustic signals. In specific embodiments the invention provides an acoustic transducer design and a method for obtaining an image by focusing a receiving portion of the transducer on a plurality of focal points and constructing the image from the received signals. Comparison with images generated from a fundamental frequency image can be used to enhance the final image.

14 Claims, 15 Drawing Sheets

METHOD AND APPARATUS FOR ULTRASOUND CONTRAST IMAGING

The present patent document is a continuation (national stage filing) of PCT Application Serial No. PCT/GB00/00115, filed Jan. 19, 2000, designating the United States and published in English, which is hereby incorporated by reference, and claims priority to the filing date of Great Britain application 9901270.0 filed Jan. 21, 1999.

The present invention relates to ultrasound contrast imaging, and more particularly to apparatus and methods for coloring enhanced images.

The invention has particular application in detecting scatter behaviour from free gas bubbles which may be present in a volume to be imaged. Such free gas bubbles may be, for example, generated in a volume of interest by introduction of ultrasound contrast imaging agents.

Ultrasound contrast agents can be introduced into the body to reflect or absorb ultrasound energy, or to resonate when exposed to such energy, and thereby provide an enhanced image of a part of the body. Examples of such contrast agents, in the form of hollow microcapsules, are given in Japanese Patent Applications Nos. 508032/1992 and 509745/1994 and in PCT/GB95/02673 (WO 96/15814). Such agents are injected into a patient's bloodstream and then the patient is subjected to ultrasound radiation.

The production of free gas bubbles from the hollow microcapsules is described in co-pending UK Patent Application No. 9800813.9.

Harmonic Imaging (HI) is therefore a well-established imaging modality for ultrasound contrast agents. Due to the nonlinear scatter behaviour an oscillating gas bubble generates multiple components of the transmitted frequency (harmonics). Under specific conditions, however, gas bubbles also backscatter subharmonics of the transmitted frequency (Neppiras; Subharmonic and other low-frequency emission from bubbles in sound-irradiated liquids. Journal Acoust Soc Am. 46: 587–601; 1996. Eller and Flynn; Generation of subharmonics of the order one-half by bubbles in a sound field. Journal Acoust Soc Am. 46 722–727; 1969). According to theory the onset of subharmonics, for a free gas bubble, depends on the transmitted frequency and the applied acoustic pressure. The acoustic pressure for the onset of subharmonics scattering is minimal at twice the resonance frequency of the gas bubble. Additionally, narrow band signals are needed because the generated subharmonic components will be more dominant when the number of periods increase.

Recently several investigators have studied the possibility for subharmonics imaging of ultrasound contrast agents (Lotsberg et al; Experimental observation of subharmonic oscillations in Infoson bubbles. Journal Acoust Soc Am. 99: 1366–1369; 1996; Shankar et al; Advantages of subharmonic over second harmonic backscatter for contrast-to-tissue echo enhancement. Ultrasound Med. Biol. 24; 395–399; 1998; Forsberg and Shi; New aspects of harmonic and subharmonic imaging. The leading edge in diagnostic ultrasound. Atlantic City; 1998). Lotsbert et al (1996) observed subharmonic scattering for Albunex. It was concluded that the acoustic pressure for the onset of subharmonics was lower than expected from the theory, as developed by Eller and Flynn (1969) where they corrected for the presence of the shell of the Albunex microspheres. The authors gave a possible explanation by assuming that because of the acoustic pressure the encapsulating shell breaks and the free air bubbles appear and will oscillate with subharmonics at a lower sound pressure. Shankar et al (1998) described the advantage of subharmonic imaging over conventional harmonic imaging concerning agent-to-tissue ratio. As function of pressure this ratio increases for the subharmonic, whereas for the second harmonic it decreases. This is probably due to the nonlinear propagation effects in tissue where second harmonic components are generated, especially at higher values of the acoustic pressure. Also, attenuation is lower for subharmonic compared to second harmonic components.

Though the harmonic nature of oscillating gas bubbles is known, subharmonics are not used in diagnostic ultrasound. This is because the characteristics are such that the resolution of subharmonic imaging is too low.

The present invention has for an object to use subharmonics in diagnostic imaging. The invention has, for a further object, to provide a new and improved transducer design and also a new and improved imaging strategy which will increase the sensitivity of the subharmonic signals and will overcome the problem of limited resolution which has heretofore prevented successful practical imaging using subharmonics.

An important advantage of using subharmonics with free gas bubbles is that the subharmonic signals are only generated from the free gas bubbles and not from any surrounding tissue and therefore an image is created of the free gas bubbles without the image from the tissue. This can be utilised to provide an enhanced image.

The present invention provides apparatus for obtaining an ultrasound image of an object, said apparatus comprising a transducer array, said transducer array including at least one first part comprising a first transducer type for transmission of ultrasound waves into the object to be imaged and at least a second part comprising a second transducer type for receiving subharmonic waves from the object being imaged, said first and second parts of said transducer being mounted adjacent to each other. Preferably each of said first and second types of said transducer comprise a plurality of transducer elements.

Preferably said apparatus further comprises means for steering the focus point of said plurality of transducer elements of said second part of said transducer to receive subharmonic signals from a plurality of points within said object.

In a specific embodiment the transducer array further comprises an additional third transducer part situated adjacent to said first transducer part on an opposite side to said second transducer part. Preferably said third transducer part is of the second transducer type.

Preferably said third transducer part is identical to said second transducer part.

Preferably said third transducer part also comprises means for steering the focus of the third transducer part to receive subharmonic signals from a plurality of points within said object.

In a further alternative embodiment, said third part is of a third transducer type, said third transducer type being sensitive to receive second harmonic signals from within said object.

Preferably said third transducer type is also steerable to focus on various points within the object.

The present invention also provides a method for ultrasonic imaging of an object, said method comprising the steps of:
i. generating a first burst of ultrasound focused into a first region of an object to imaged;
ii. receiving first subharmonic ultrasonic signals from plurality of first focus points within said first region of said object;

iii. receiving at least second subharmonic ultrasonic signals for said at least second region of said object to be imaged;

iv. storing said first and at least second subharmonic ultrasonic signals; and v. processing said first and at least second stored signals to produce an image of said object.

Preferably said processing of said image of said object also comprises comparison of said image produced from said subharmonic signals with fundamental output signals from the same region of said object.

Preferably said method further comprises receiving second harmonic signals from said first and said at least second region of said object and storing said second harmonic signal output, said processing comprising comparing the subharmonic and second harmonic output signals to produce an enhanced image of said object.

In a preferred embodiment the first burst of ultrasound comprises two or more portions, a first preparation portion and a second imaging portion at a different amplitude or frequency from said first preparation portion. The first preparation portion comprises a pulse burst which does not generate substantial subharmonics but is of an amplitude or frequency which creates a rapid onset of subharmonics in the imaging portion.

The present invention therefore also provides a method of ultrasonic imaging of an object, said method comprising the steps of generating a burst of ultrasound focused into a region of said object to be imaged, said burst of ultrasound comprising two or more portions, a first preparation portion and a second portion at a different amplitude or frequency from said first preparation portion, said burst being designed to generate subharmonics within said object.

Embodiments of the present invention will now be described, by way of example with reference to the accompanying drawings in which.

The present invention will now be described with reference to the accompanying drawings which provide an explanation of the principles of the present invention and also provide examples of the transducer designs and ultrasonic imaging methods.

Figure 1:
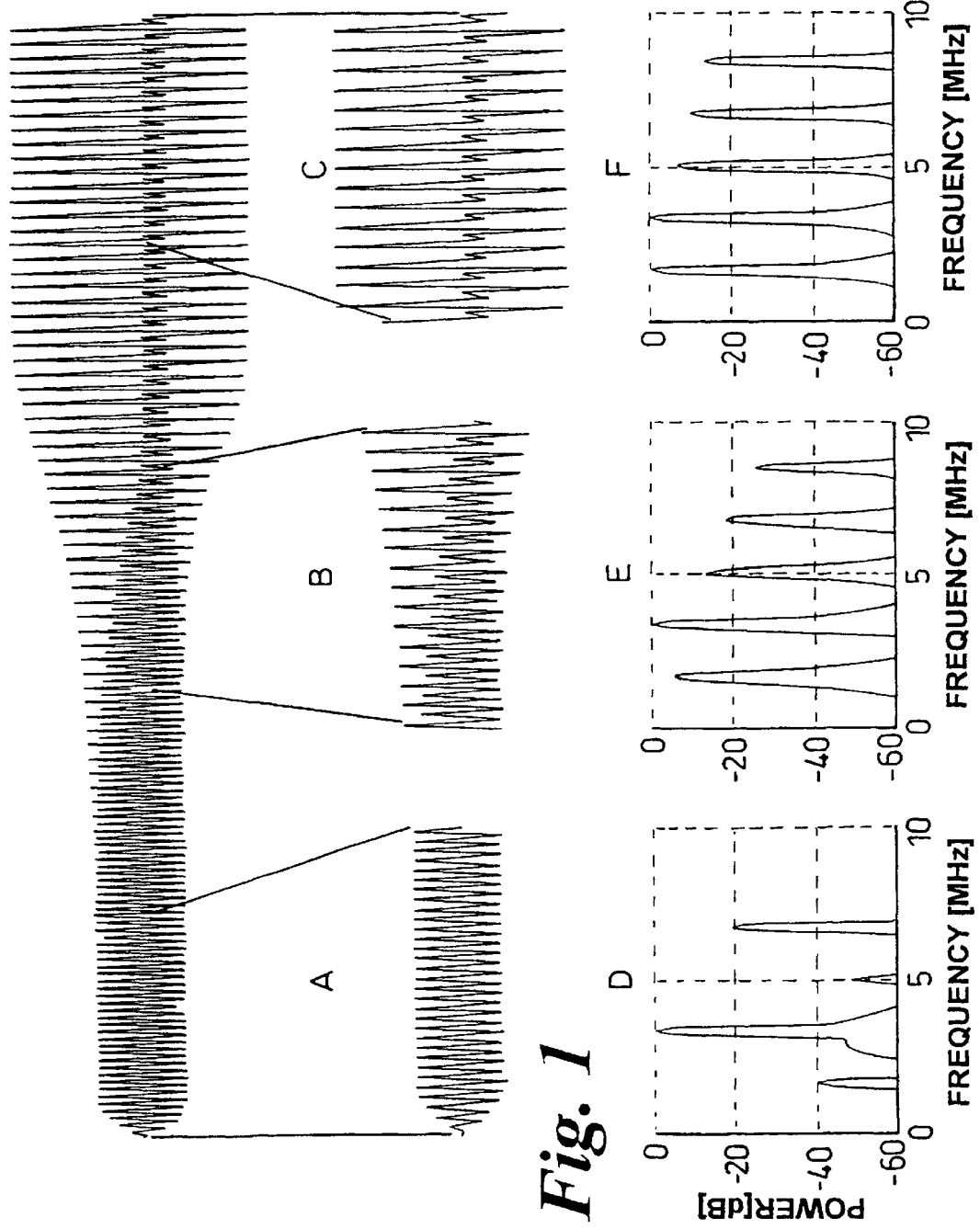
FIG. 1 shows a graph of bubble wall velocity as a function of time and corresponding scatter spectra.

To demonstrate the presence of subharmonics, simulations were performed by using the Rayleigh-Plesset equation as a free gas bubble model. Damping and surface tension was included. FIG. 1 (top) shows the bubble wall velocity as function of time of a single microsphere with a diameter of 4 $\mu$m, in response to a 3.38 MHz sine burst of 150 periods with amplitude of 175 kPa. The growth of the subharmonic component is shown by the 3 different time stages (A–C) of the bubble wall velocity, with their corresponding scatter spectra (D–F), FIG. 1 bottom.

The applied frequency of the sine burst was set to 3.38 MHz because this is twice the resonance frequency for a 4 $\mu$m microsphere. At this frequency the acoustic pressure threshold should be minimal for subharmonic generation. From FIGS. 1D–F it can be concluded that mainly the subharmonic components increase in time.

Figure 2:
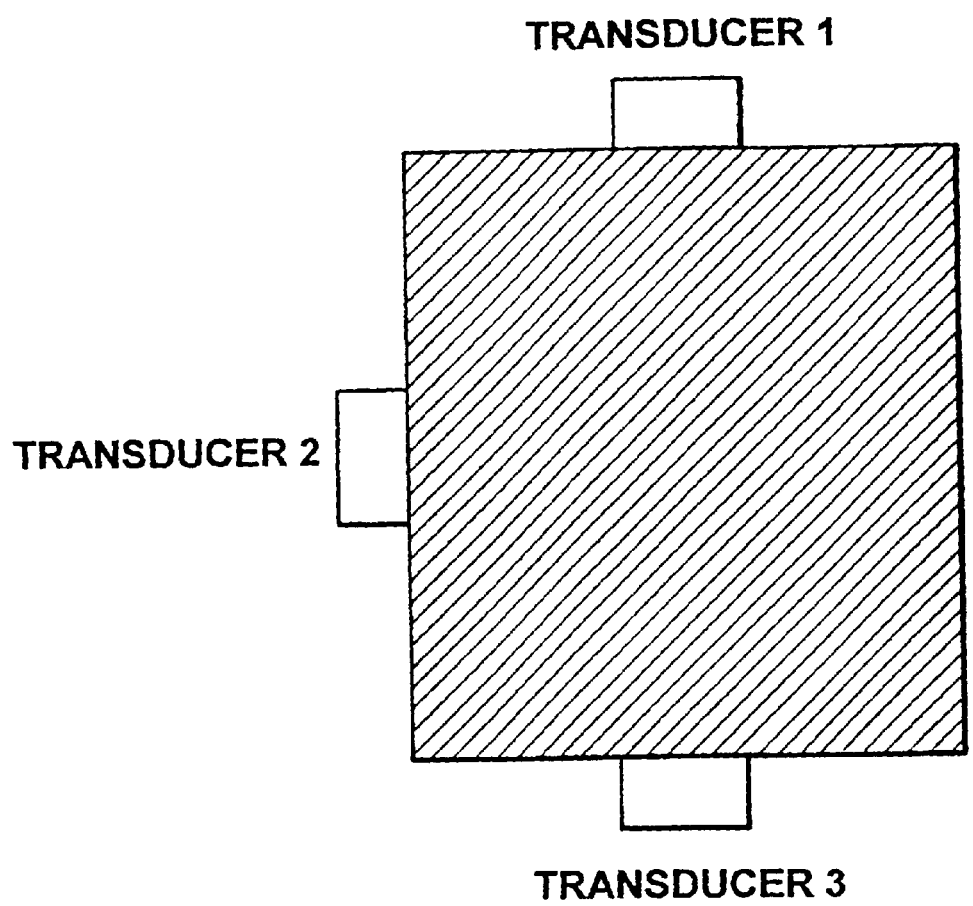
FIG. 2 shows the measurement set up with a three element transducer.

Measurements of subharmonics were taken with Quantison microcapsules. Quantison is defined in co-pending UK Patent Application No. 9800843.9 which refers to several published documents. The measurement set-up of FIG. 2 was used: In this set-up 3 single element transducers are used. Transducer 1 has a frequency of 0.5 MHz and a high acoustic pressure and causes the gas to release from the Quantison microspheres. Transducer 2 has a frequency of 5 MHz and is used to transmit a burst of 5 MHz. The burst is typical 30 periods long. Transducer 3 is used as a broadband receiver, which is sensitive between 1 and 10 MHz.

Figure 3:
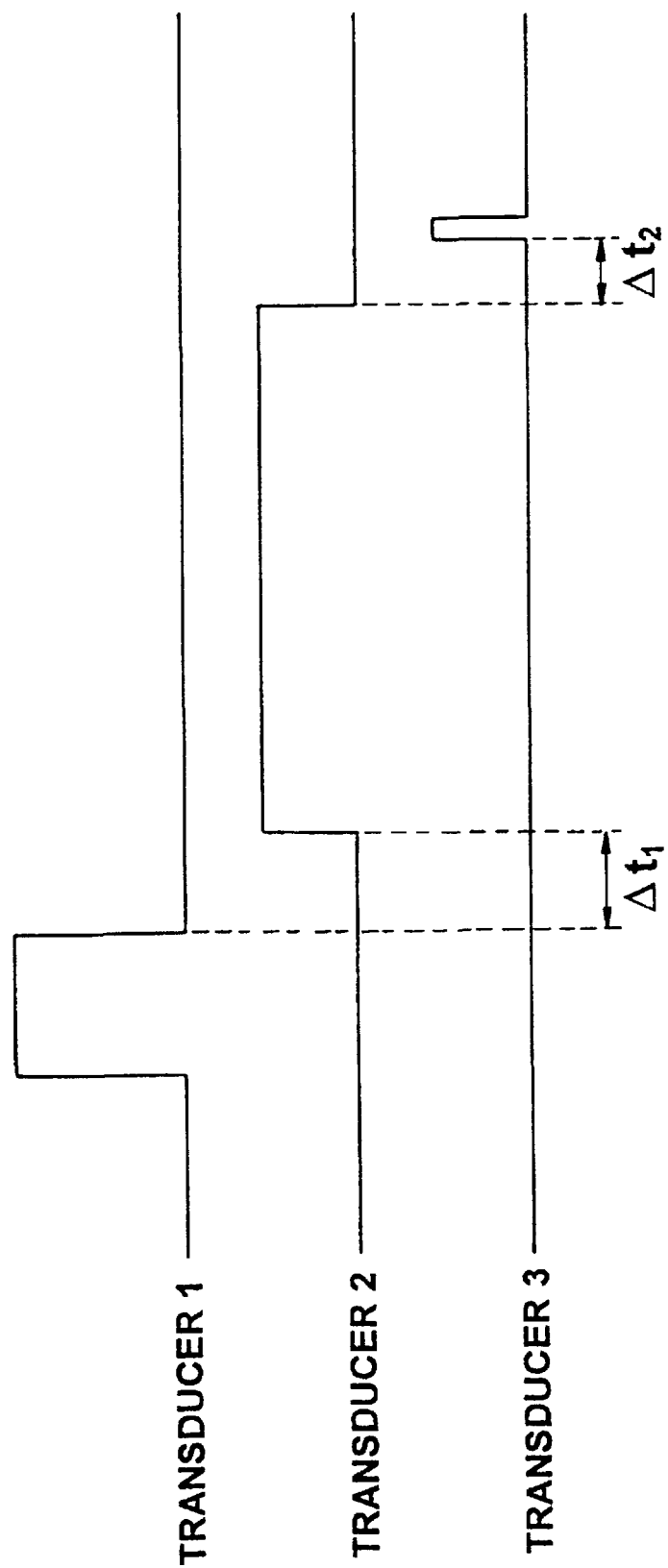
FIG. 3 shows a timing diagram for the three element transducer of FIG. 2.

FIG. 3 gives the timing of the different transducers.

$0 < \Delta t_1 < 10$ ms for Quantison $\Delta t_2$ is depending on the scanning depth (0–2001 $\mu$s)

Figure 4:
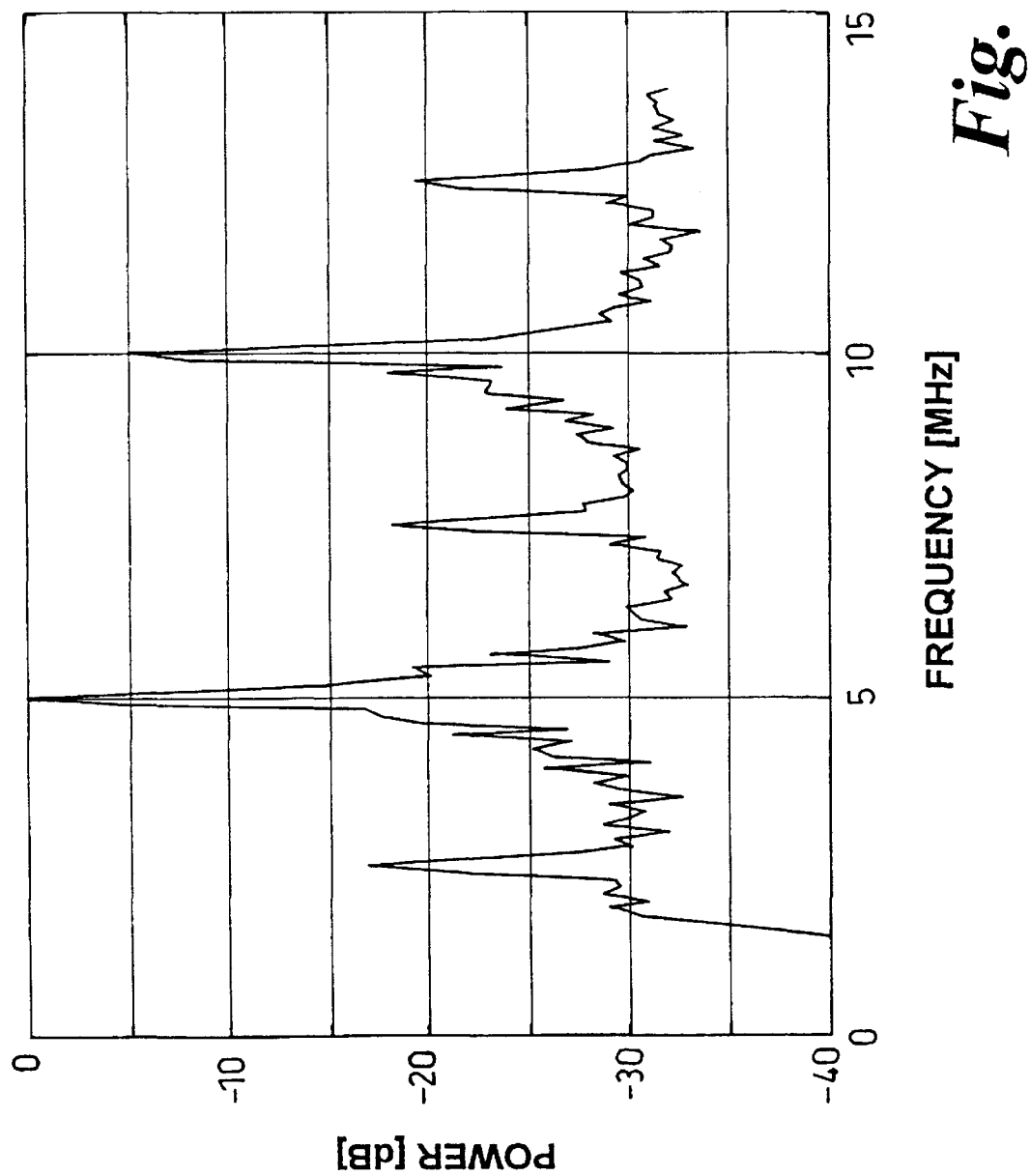
FIG. 4 shows the scatter spectrum of the bubbles under investigation.

FIG. 4 gives the result as received with transducer 3 when the transmit frequency of transducer 2 is 5 MHz. In the figure peaks are located at the fundamental frequency, 5 MHz. The subharmonic peak is located at 2.5 MHz, while the ultraharmonic is at 7.5 MHz and the second harmonic at 10 MHz.

In the experiment with Quantison transducer 1 has a frequency of 0.5 MHz. Free gas-bubbles are created which measure about 2.8 $\mu$m in diameter. The resonance frequency for such a bubble is approximately 2.5 MHz. From the literature it is known that for subharmonics, the most ideal isonifying frequency is 2 times the resonance frequency. That is why 5 MHz is used for transducer 2.

Figure 5:
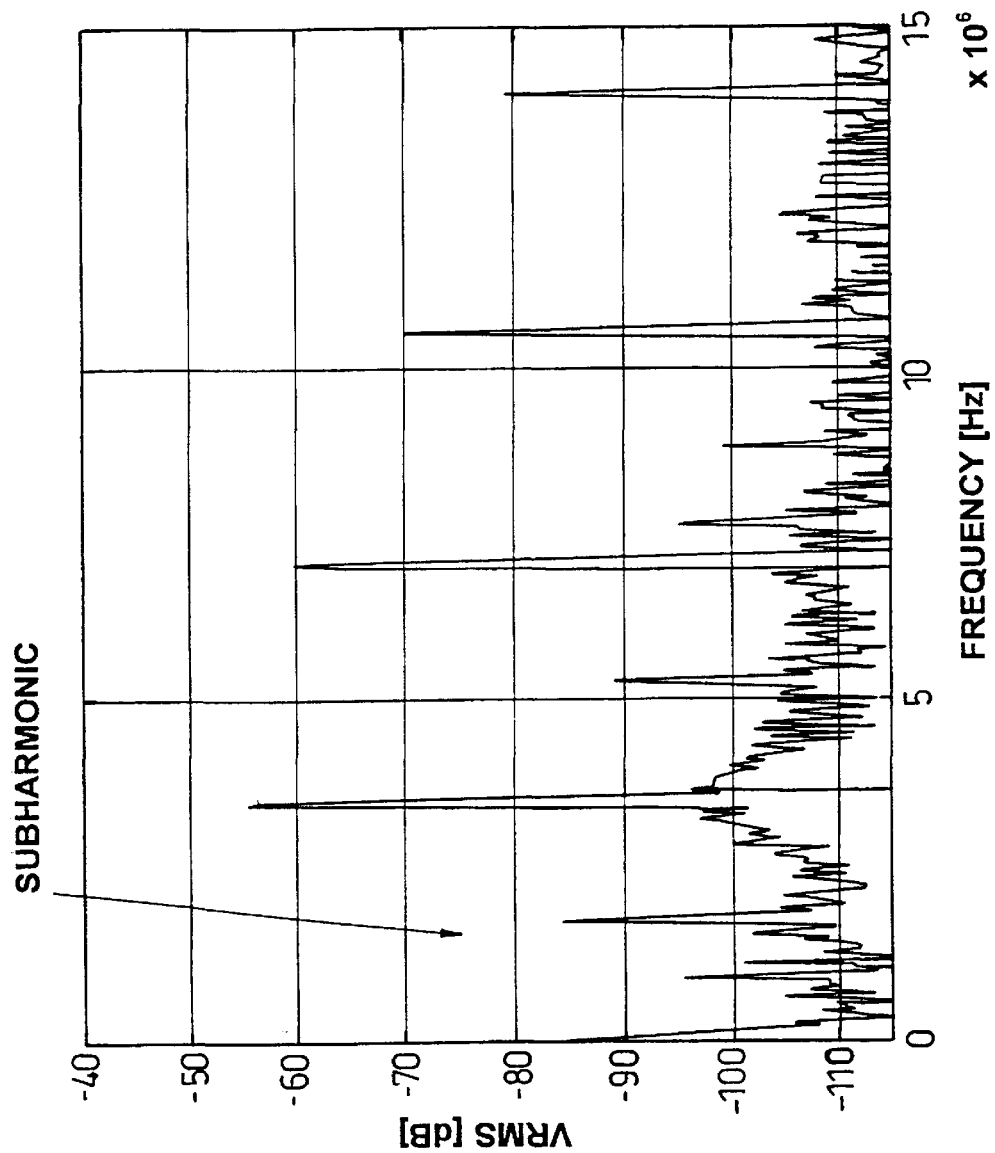
FIG. 5 shows an amplitude spectrum of the received signal as the, response of a pulsed sinusoidal signal of 3.5 MHz transmitted through a bubble cloud of Infoson.

Subharmonics are known in the field. It has been measured by several investigators like Lotsberg (1996) who observed subharmonics in Infoson. FIG. 5 shows a graph from that article. From this article it is shown that transducer 1 and 2 can be the same transducer.

The inventors have realised that there are certain subharmonic imaging limitations. Firstly, a long burst is required to generate the subharmonics. The longer the burst the more dominant the subharmonics. A typical value is 50 periods. With 50 periods the resolution in depth is about 1–3 cm depending on the used frequency. Secondly, the transducer has to be broadbanded. First to transmit the ultrasound wave at frequency f0 and secondly to receive the subharmonic at ½ f0.

The present invention provides a new transducer specifically designed for subharmonic imaging and also a new scanning protocol specially for subharmonic imaging.

Figure 6:
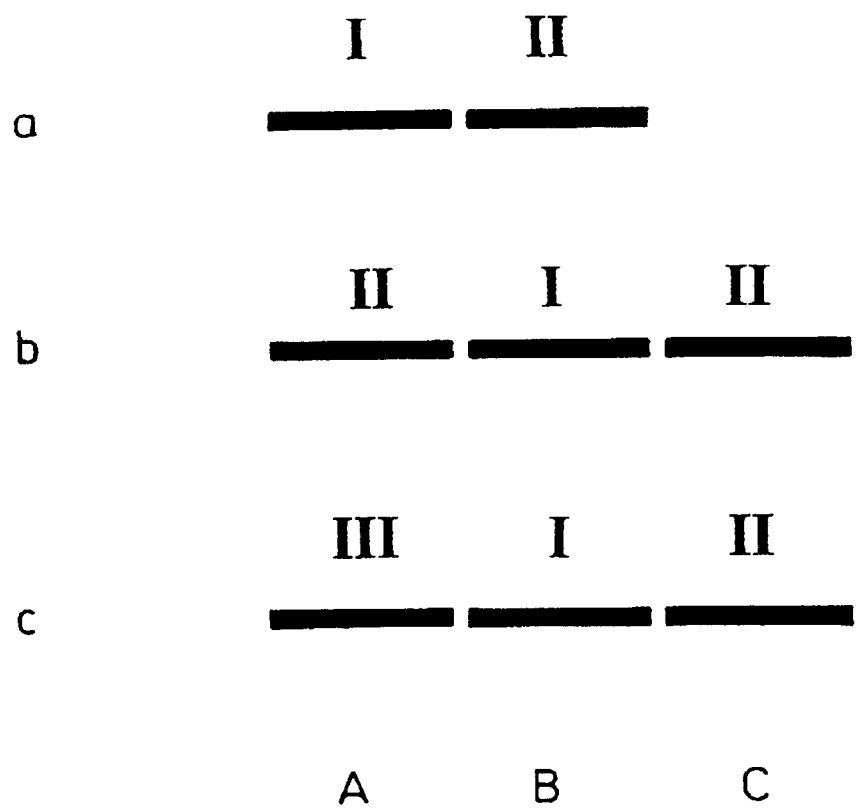
FIG. 6 shows the measurement set up with three transducer designs according to the present invention.

The three transducer types are shown in FIG. 6.

a. The array transducer for cardiac imaging measures about 2 cm. The number of elements is typical 96, 128 or 256. The array is split in two main parts A and B. Part A is used to transmit the ultrasound wave. Part B is used to receive the subharmonics. Part A consist of a type I transducer transmitting the frequency fO. Part B consist of type II transducer which is sensitive to the subharmonics at 0.5×fO. Type I transducer has typical 32–128 elements. Type II transducer has typically 32–128 elements.

b. The transducer consists of 3 parts. The middle part of type I transducer, the two outer parts type II.

c. The transducer consist of 3 parts. The middle part is type I transducer. One outer part is type II, the other outer part is type III.

Type III has typical 32–128 elements. Type III is sensitive for 2×fO.

Type I is a normal broadband transducer or a dual frequency transducer as described in co-pending UK Patent Application No. 9800813.9.

Figure 7:
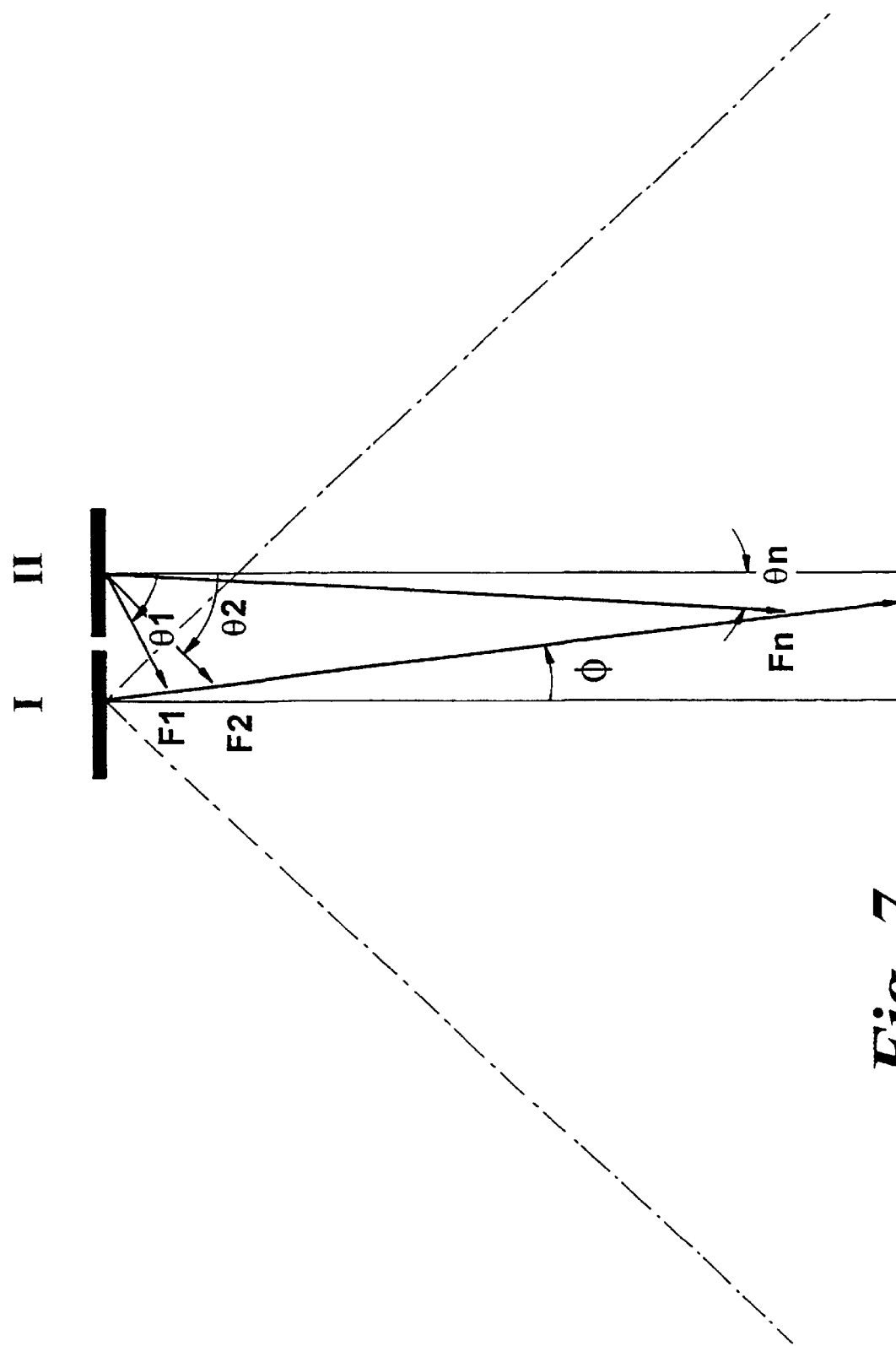
FIG. 7 shows diagrammatically the operation of one of the transducer designs of FIG. 6.

The scanning procedure is described with reference to FIGS. 7 to 10. With reference to FIG. 7, the type I transducer is a phased array transducer and able to make a sector image. The ultrasound direction can be. steered (normally between −45 and 45 degrees). The type I transducer generates a burst typically 50–100 periods. The type II transducer can also be steered (in reception).

The type I transducer generates a burst in the direction of $\phi$. The type II transducer starts with receiving the subharmonic at angle $\theta_1$ and focused on point F1. As the ultrasound wave propagates along the line the type II transducer changes the receiving angle and focus to $\theta_2$ and F2 respectively, until the highest depth is reached for $\theta_n$ and Fn.

By changing the angle $\phi$ between −45 and 45 degrees a whole sector can be scanned in this way.

For a transducer as shown in FIG. 6b transducer C is used for $\phi$ between 0 and 45 degrees. Transducer A is used for $\phi$ between 0 and −45 degrees. Using transducer A and C at the same time will further improve the resolution.

Figure 8:
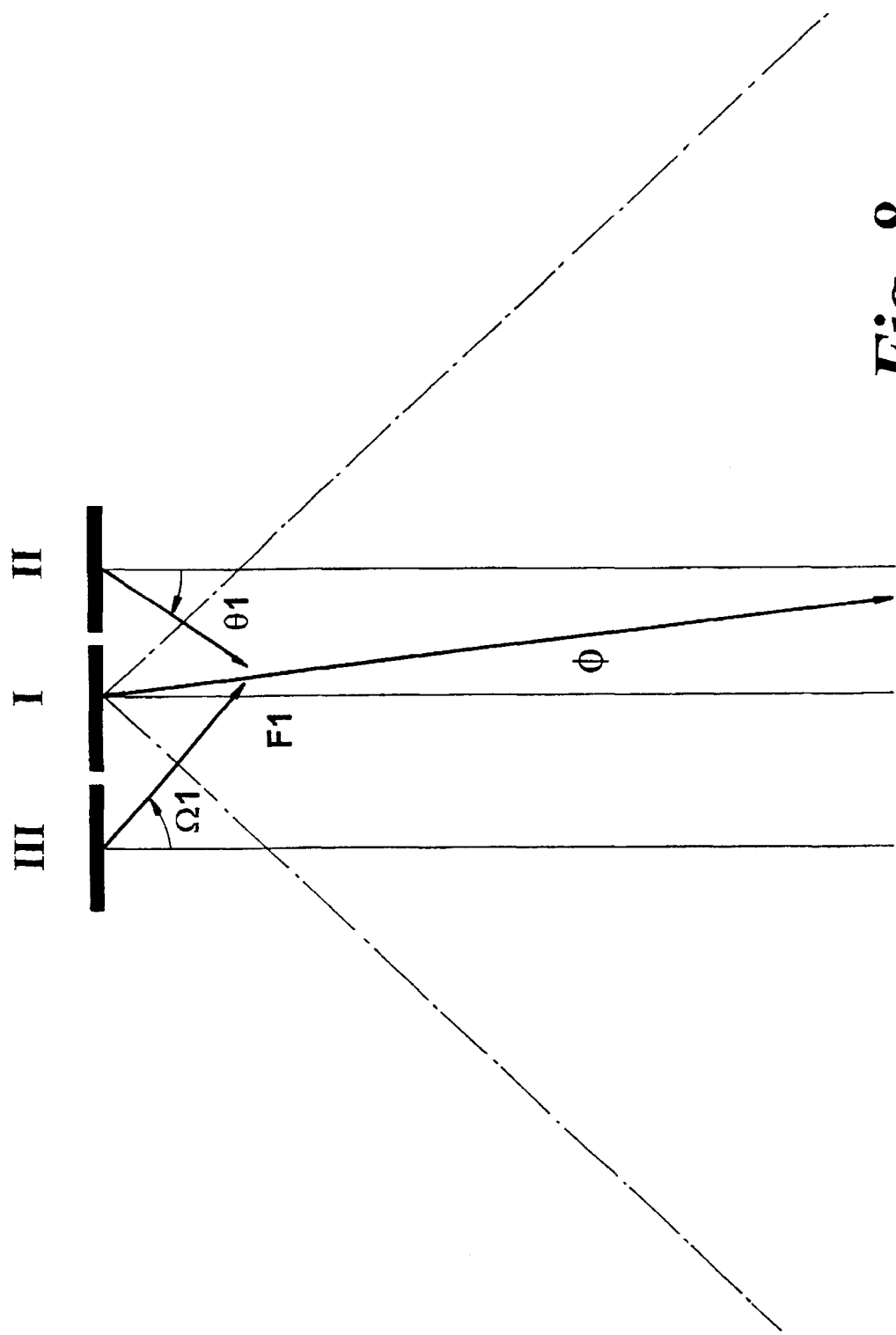
FIG. 8 shows diagrammatically the operation of a further one of the transducer designs of FIG. 6.

For a transducer as shown in FIG. 6c, as shown in FIG. 8, the type I transducer. generates a burst in the direction of $\phi$. The type II transducer starts with receiving the subharmonic at angle $\theta_1$ and focused on Point F1.

The type III transducer starts with receiving the second harmonic at angle $\Omega_1$ and focused on Point F1.

As the ultrasound wave propagates along the line the type II and the type III transducer changes the receiving angle and focus until the highest depth is reached.

For cardiac imaging the distance between the centres of the transducer part in FIG. 6 is typical 1 cm. For radiology this can be increased up to 5 cm, which will increase the resolution.

The subharmonic image will contain only data from the bubble generation since the object tissue will not generate subharmonics.

The subharmonic information may be combined with the conventional 2D ultrasound image fundamental or harmonic in several ways. Reference is made to UK Patent Application No. 9800813.9 for an example of how to combine the images to produce an enhanced image.

Figure 9:
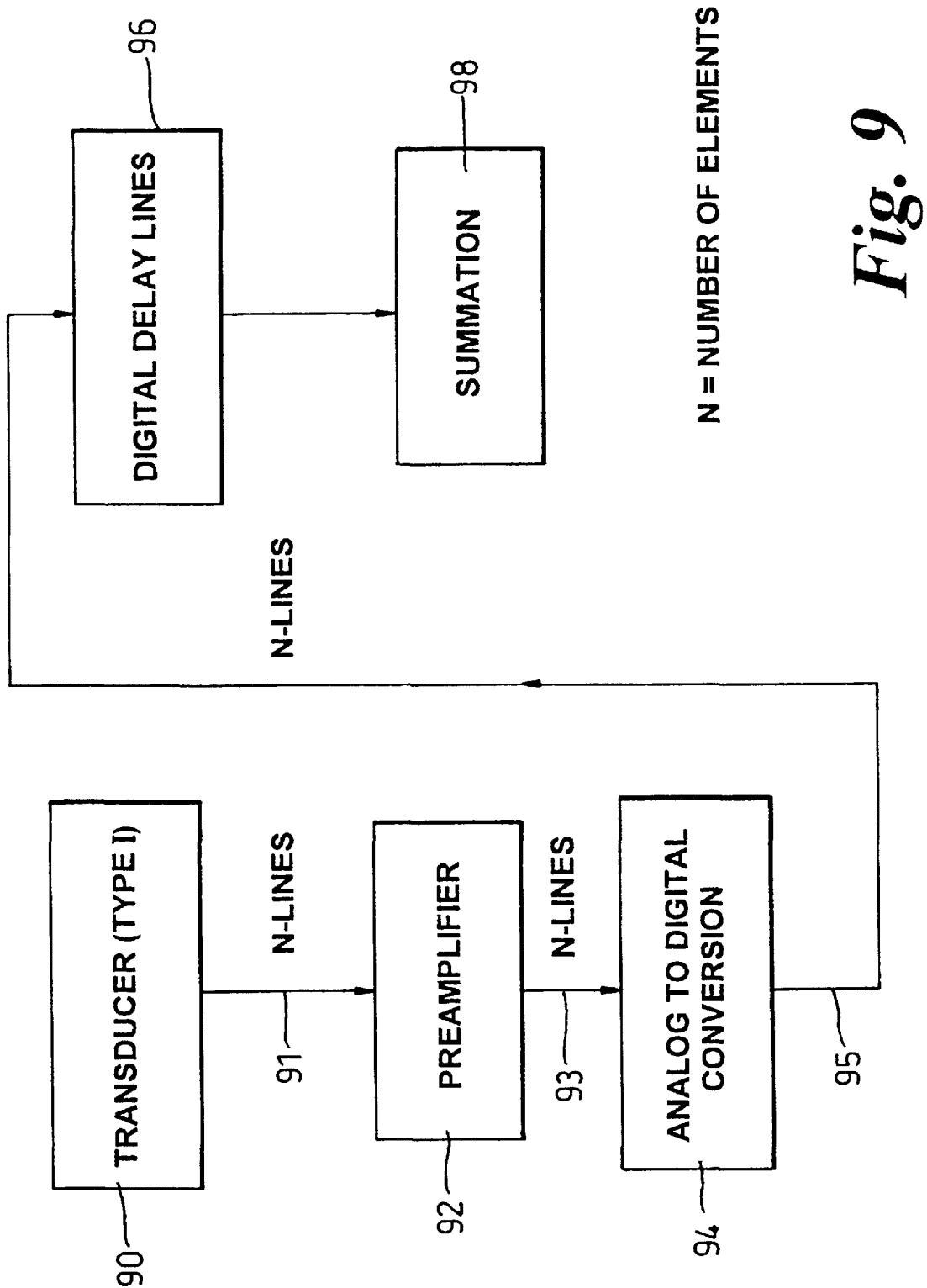
FIG. 9 shows a block diagram of the control electronics for the transducer arrangement of FIG. 6.
Figure 10:
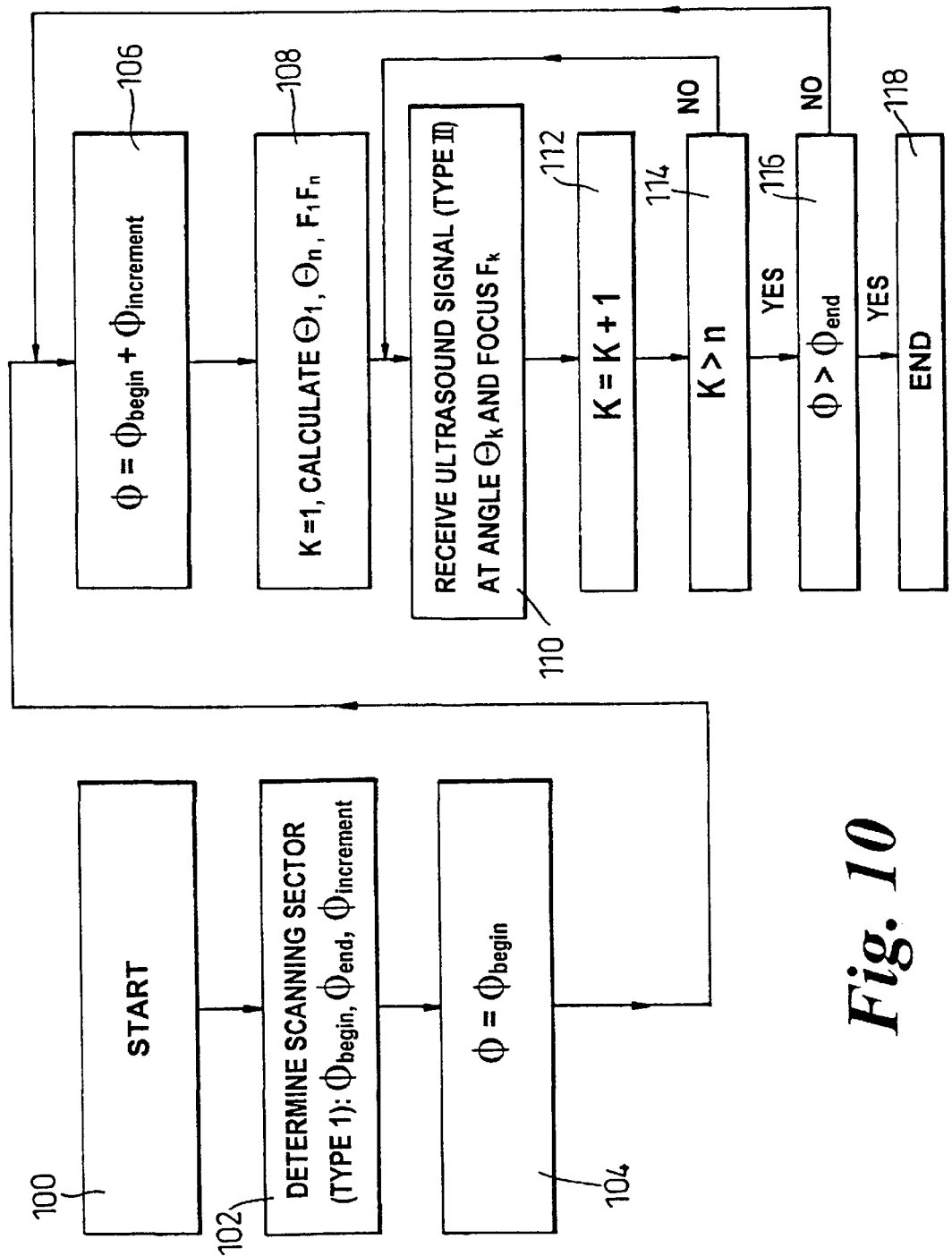
FIG. 10 shows a flow diagram for the transducer arrangement of FIG. 6.

With reference now to FIGS. 9 and 10, FIG. 9 shows a block schematic diagram of the electronics which are shown as an example for transducer type I(90).

Transducer 90 is connected to a preamplifier 92 via N-lines 91, preamplifier 92 amplifying the analogue output signals of the elements of transducer 90 and feeding the amplified output to an analogue to digital converter 94, again via an N-line link 93.

The digital outputs of analogue to digital converter 94 are fed via N-lines 95 to a digital delay line circuit 96 and then to a summation circuit 98.

An exemplary flow diagram for subharmonic imaging is shown in FIG. 10. From a start 100 the scanning sector is determined 102 and sequential scanning is commenced, 104.

In step 106 the angle is incremented once a measurement sequence, as described in steps 108 to 116, is completed.

In step 116 the angle $\phi$ is incremented (step 106) but if the angle has reached the limit then the sequence is completed (step 118).

With reference to FIGS. 11 to 15, an alternative imaging pulse sequence for generating subharmonics is shown.

In this new transmit burst for generating subharmonics the burst consists of 2 (or more) parts. The first part is called the PREPARATION burst and the second part is called the IMAGING burst. The PREPARATION burst differs (beside the length) from IMAGING burst in amplitude and/or frequency. The PREPARATION burst does not (or only at a very low level) generate subharmonics itself, but causes a very rapid onset of subharmonics in the IMAGING burst.

Figure 11:
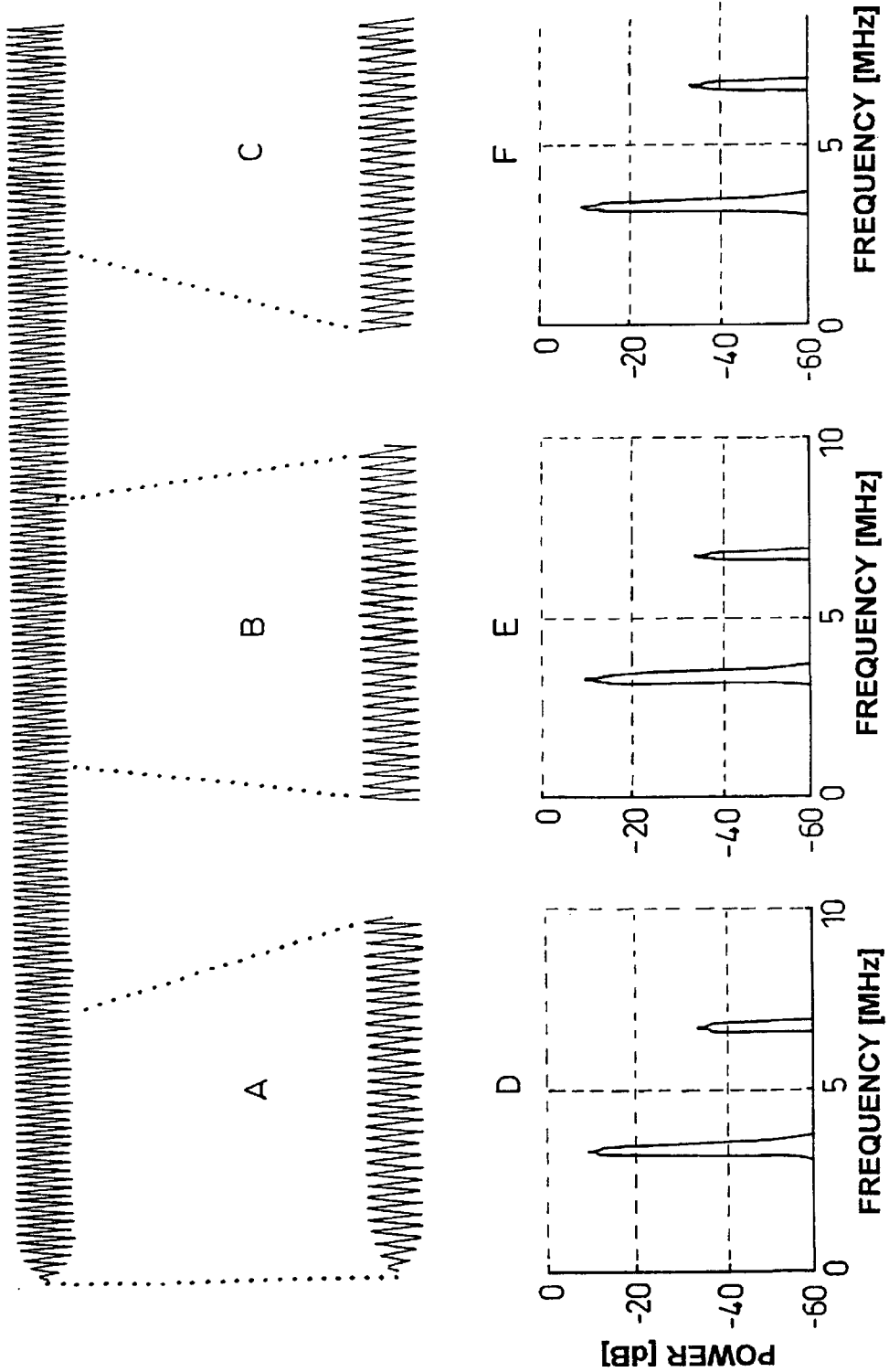
FIG. 11 shows a further graph of bubble wall velocity as a function of time and a further corresponding scatter spectra.

FIG. 11 shows that a burst at an amplitude of 100 kPascal does not cause any subharmonics. It is the same simulation as performed for FIG. 1, except that the amplitude is now 100 kPascal instead of 175 kPascal as in FIG. 1.

Figure 12:
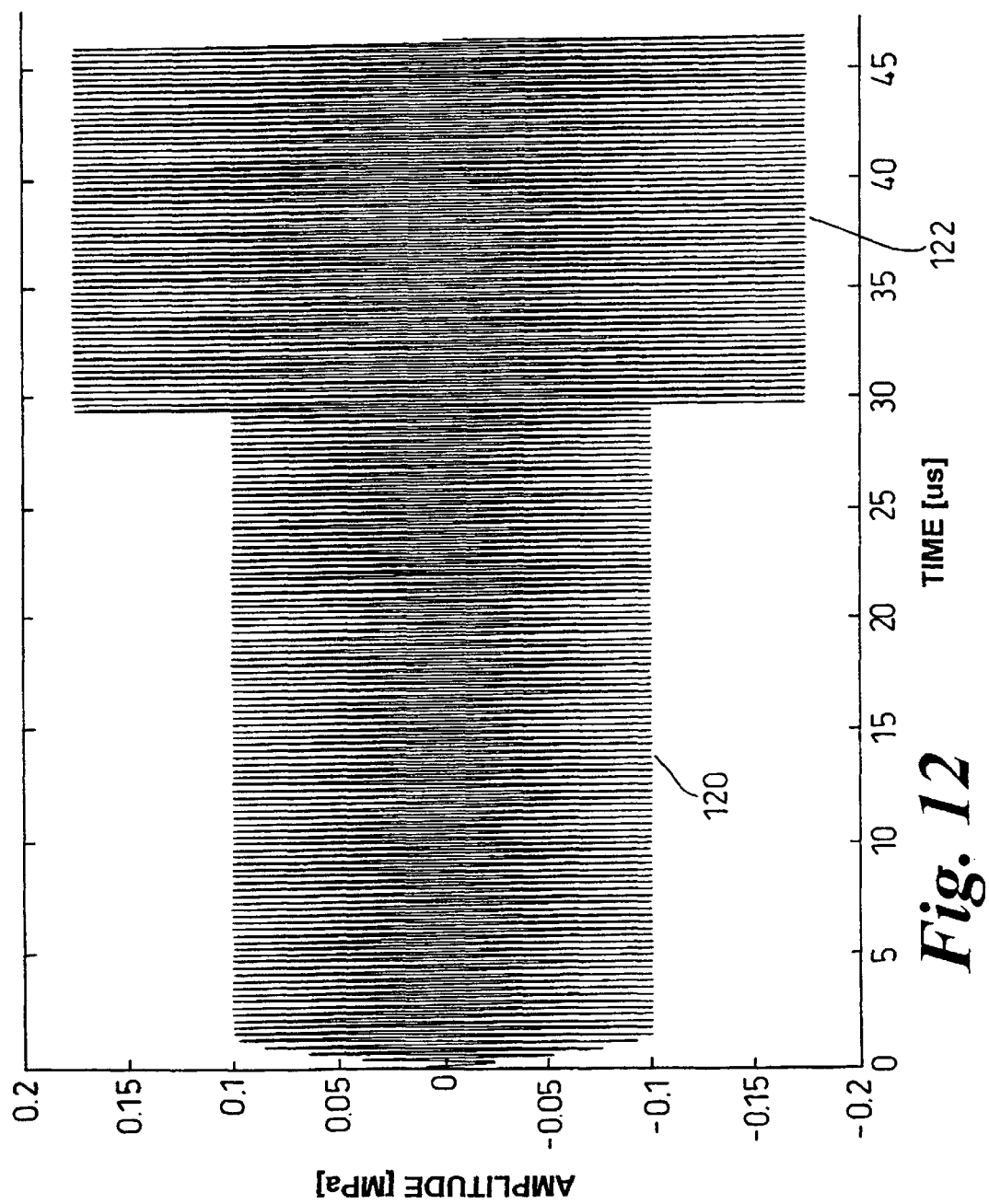
FIG. 12 shows an exemplary first preparation burst followed by an imaging burst in accordance with a further embodiment of the present invention.

In FIG. 12 the PREPARATION burst 120 is 100 periods and relatively low amplitude (100 kPa) with a frequency of 2*fO, followed by a IMAGING burst 122 of 50 periods with an amplitude of 175 kPa at the same frequency (3.5 MHz).

Figure 13:
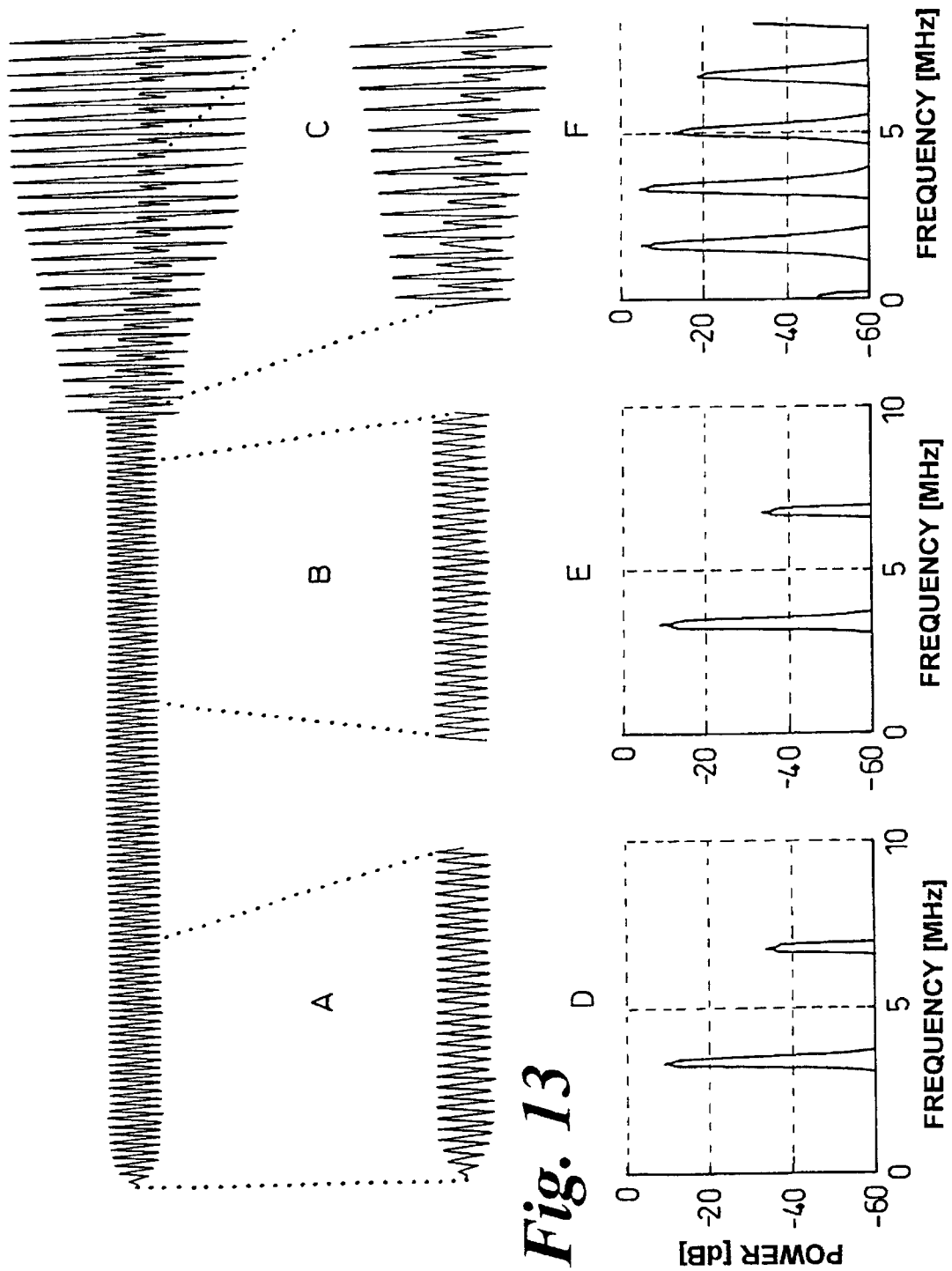
FIG. 13 shows a graph of bubble wall velocity as a function of time and a further corresponding scatter spectra for a pulse burst sequence as shown in FIG. 12.

FIG. 13 shows the simulation results. A and B does not show any subharmonics as shown in E and D. The peaks shown in E and D are located at 3.5 and 7 MHz which are the fundamental and the second harmonic respectively. Directly after the amplitude has raised to 175 kPascal subharmonics show up. This is shown in trace C and in the frequency plot F. In plot F subharmonics are shown at 1.75 MHz and ultraharmonics at 5.25, 8.75 MHz etc.

Figure 14:
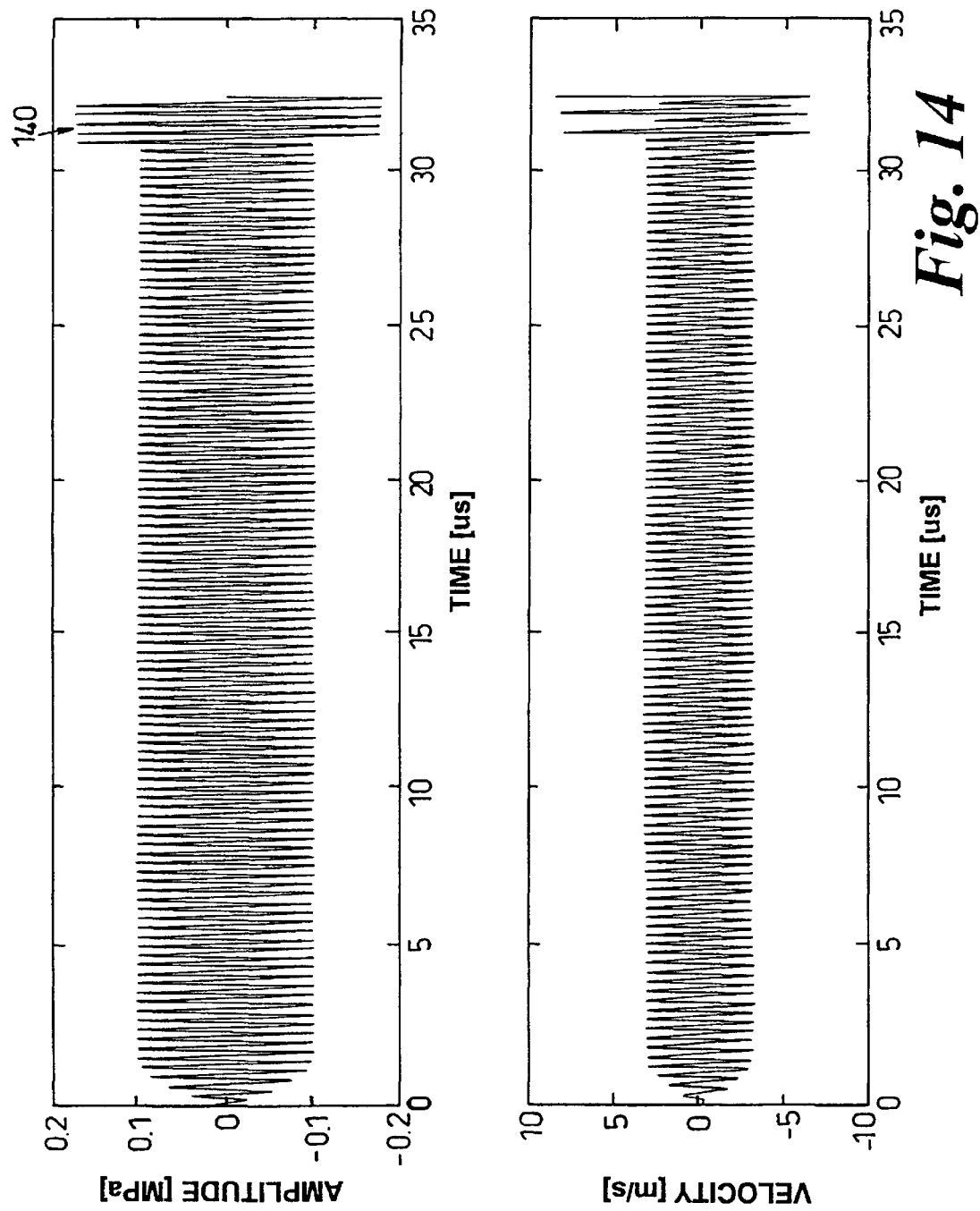
FIG. 14 shows an exemplary transmitting burst and a time trace.

FIG. 14 (top) shows a transmitting burst of which the IMAGING part 140 is only 5 periods. At the bottom the time trace is shown as a result of the simulation of the bubble wall velocity.

Figure 15:
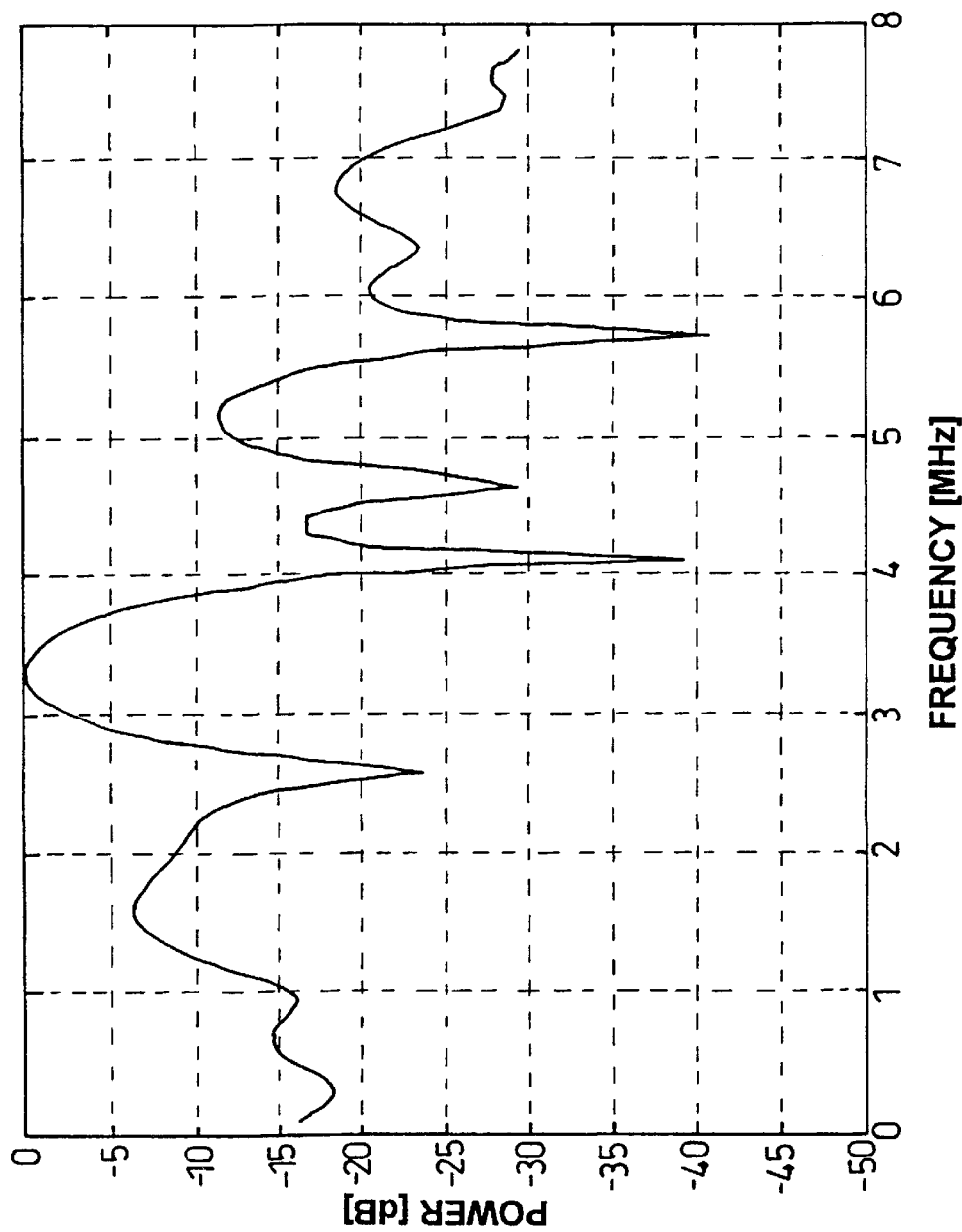
FIG. 15 shows a frequency response for the transmitting burst of FIG. 14.

FIG. 15 shows the frequency response of the 5 periods of the IMAGING part. Subharmonics are clearly seen at 1.7 MHz and ultraharmonics at 5.25 MHz.

For the imaging procedure the transducer (type I) transmit a burst which consist of a PREPARATION part and an IMAGING part. The PREPARATION part has, e.g. 100 periods but can be as short as one or a few periods. The IMAGING part, e.g. 5 periods (see FIG. 15).

With this relatively short imaging part subharmonics are generated. So high resolution with subharmonic imaging is obtained.

The scanning protocol can be the same as described before.

The receiving transducer and electronics is sensitive for the subharmonic frequency and relative insensitivity for the fundamental frequency. So the receiving transducer and electronics are insensitive for the relative long PREPARATION burst, but sensitive for the relatively short IMAGING burst if there is contrast agent and/or gas bubbles present which generates subharmonics. These objects are then imaged with a high resolution.

In the described example the PREPARATION part differs from the IMAGING part in acoustic amplitude and length, but have the same frequency. Systems are possible in which the frequency is different and the amplitude is the same or in which both amplitude and frequency varies. Also, systems are possible in which the amplitude of the imaging part is lower than the preparation part.

The change in amplitude or frequency or both between the preparation and imaging parts of the signal are found to generate subharmonics due to the rapid change.

Using separate transducers for transmitting and receiving will give the best performance in terms of axial resolution. When using the same transducer for transmitting and receiving, no receiving signals can be acquired as long as the transducer is in the transmitting mode.

The different transducers may have the same centre, because axial resolution is now determined by the resolution in the time signal.

What is claimed is:

1. Apparatus for obtaining an ultrasound image of an object, said apparatus comprising a transducer array, said transducer array including at least one first part comprising a first transducer type for transmission of ultrasound waves into the object to be imaged and at least a second transducer type for receiving subharmonic waves from the object being imaged, said first and second parts of said transducer being mounted adjacent to each other;

wherein the transducer array further comprises an additional third transducer part situated adjacent to said first transducer part on an opposite side to said second transducer part.

2. Apparatus as claimed in claim 1 in which each of said first and second types of said transducer comprise a plurality of transducer elements.

3. Apparatus as claimed in claim 1 or claim 2 in which said apparatus further comprises means for steering the focus point of said plurality of transducer elements of said second part of said transducer to receive subharmonic signals from a plurality of points within said object.

4. Apparatus as claimed in claim 1 in which said third transducer part is of the second transducer type.

5. Apparatus as claimed in claim 4 in which said third transducer part is identical to said second transducer part.

6. Apparatus as claimed in claim 5 in which said third transducer part also comprises means for steering the focus of the third transducer part to receive subharmonic signals from a plurality of points within said object.

7. Apparatus as claimed in claim 1 in which said third part is of a third transducer type, said third transducer type being sensitive to receive second harmonic signals from within said object.

8. Apparatus as claimed in claim 7 in which said third transducer type is steerable to focus on various points within the object.

9. A method for ultrasonic imaging of and object, said method comprising:
   i. generating a first burst of ultrasound focused into a first region of an object to be imaged;
   ii. receiving first subharmonic ultrasonic signals from a plurality of first focus points within said first region of said object;
   iii. receiving at least second subharmonic ultrasonic signals for a at least second region of said object to be imaged;
   iv. storing said first and at least second subharmonic ultrasonic signals; and
   v. processing said first and at least second stored signals to produce an image of said object.

10. A method of ultrasonic imaging as claimed in claim 9 in which said processing of said image of said object also comprises comparison of said image produced from said subharmonic signals with fundamental output signals from the same region of said object.

11. A method of ultrasonic imaging as claimed in claim 9 said methods further comprising receiving second harmonic signals from said first and said at least second region of said object and storing said second harmonic signal output, said processing comprising comparing the subharmonic and second harmonic output signals to produce an enhanced image of said object.

12. A method of ultrasonic imaging as claimed in any one of claims 9 to 11 in which the first burst of ultrasound comprises two or more portions, a first preparation portion and a second imaging portion at a different amplitude or frequency from said first preparation portion.

13. A method of ultrasonic imaging as claimed in claim 12 in which the first preparation portion comprises a pulse burst which does not generate substantial subharmonics but is of an amplitude or frequency which creates a rapid onset of subharmonics in the imaging portion.

14. A method of ultrasonic imaging of an object, said method comprising the steps of generating a burst of ultrasound focused into a region of said object to be imaged, said burst of ultrasound comprising two or more portions, a first preparation portion and a second portion at a different amplitude or frequency from said first preparation portion, said burst being designed to generate subharmonics within said object.

* * * * *